US012721756B2

(12) United States Patent
Wang et al.

(10) Patent No.: US 12,721,756 B2
(45) Date of Patent: Sep. 1, 2026

(54) ABSORBENT COMPOSITES

(71) Applicant: Berry Global, Inc., Evansville, IN (US)

(72) Inventors: Lei Wang, Mooresville, NC (US); Nyle Bishop, Mooresville, NC (US); Gregory Wagner Farell, Hendersonville, TN (US); Pierre Grondin, Mooresville, NC (US)

(73) Assignee: MAGNERA CORPORATION, Charlotte, NC (US)

( * ) Notice: Subject to any disclaimer, the term of this patent is extended or adjusted under 35 U.S.C. 154(b) by 517 days.

(21) Appl. No.: 16/038,538

(22) Filed: Jul. 18, 2018

(65) Prior Publication Data

US 2019/0021913 A1 Jan. 24, 2019

Related U.S. Application Data

(60) Provisional application No. 62/534,274, filed on Jul. 19, 2017.

(51) Int. Cl.
*A61F 13/15* (2006.01)
*A61F 13/51* (2006.01)
(Continued)

(52) U.S. Cl.
CPC ...... *A61F 13/15203* (2013.01); *A61F 13/511* (2013.01); *A61F 13/51121* (2013.01);
(Continued)

(58) Field of Classification Search
CPC .............. A61F 13/15203; A61F 13/511; A61F 13/51121; A61F 2013/15073;
(Continued)

(56) References Cited

U.S. PATENT DOCUMENTS 5,114,787 A * 5/1992 Chaplin .................... B32B 5/26 442/361
5,342,338 A * 8/1994 Roe ....................... A61F 13/511 604/383

(Continued)

FOREIGN PATENT DOCUMENTS

CA 2408524 A1 11/2001
JP H05261126 A 10/1993

(Continued)

OTHER PUBLICATIONS

Second Written Opinion of PCT/US2018/042676 mailed on Jun. 6, 2019, all enclosed pages cited herein.

(Continued)

*Primary Examiner* — Jenna N Chandhok
(74) *Attorney, Agent, or Firm* — BURR & FORMAN

(57) ABSTRACT

Absorbent composites are provided that include a nonwoven top layer having hydrophilic fibers and an absorbent core layer directly or indirectly attached to the nonwoven top layer, wherein the absorbent core layer comprises a through-air-bonded nonwoven. The absorbent composites may include a combination of (i) a composite-run-off value of less than 50% as determined by ISO 9073-11, (ii) a composite-absorption capacity of at least 600% as determined by ISO 9073, and (iii) a composite-rate of absorption of less than 10 seconds for a 5 ml liquid sample as determined by D824-94. The absorbent composites may include an optional film layer attached to the absorbent core layer.

25 Claims, 2 Drawing Sheets

(51) Int. Cl.

| | |
|---|---|
| ***A61F 13/511*** | (2006.01) |
| ***A61F 13/513*** | (2006.01) |
| ***A61F 13/514*** | (2006.01) |
| ***A61F 13/53*** | (2006.01) |
| ***A61F 13/539*** | (2006.01) |
| ***B32B 5/02*** | (2006.01) |
| ***B32B 5/26*** | (2006.01) |
| ***B32B 27/12*** | (2006.01) |

(52) U.S. Cl.

CPC ...... *A61F 13/513* (2013.01); *A61F 13/51401* (2013.01); *A61F 13/53* (2013.01); *A61F 13/539* (2013.01); *A61F 2013/15073* (2013.01); *A61F 2013/15447* (2013.01); *A61F 2013/15471* (2013.01); *A61F 2013/15552* (2013.01); *A61F 2013/51033* (2013.01); *A61F 2013/51355* (2013.01); *A61F 2013/51409* (2013.01); *A61F 2013/53024* (2013.01); *A61F 2013/530299* (2013.01); *A61F 2013/53908* (2013.01); *A61F 2013/5395* (2013.01); *A61F 2013/53991* (2013.01); *B32B 5/022* (2013.01); *B32B 5/26* (2013.01); *B32B 27/12* (2013.01); *B32B 2250/02* (2013.01); *B32B 2250/03* (2013.01); *B32B 2307/7265* (2013.01); *B32B 2307/728* (2013.01); *B32B 2535/00* (2013.01)

(58) Field of Classification Search

CPC .......... A61F 2013/51033; A61F 2013/530226; A61F 2013/530299; B32B 5/23; B32B 27/12; B32B 2250/02; B32B 2250/03; B32B 2307/728; B32B 5/022

See application file for complete search history.

(56) References Cited

U.S. PATENT DOCUMENTS 5,509,915 A * 4/1996 Hanson ............. A61F 13/15203 604/378
5,951,535 A * 9/1999 Fujiwara ................ D04H 1/542 604/384
6,096,015 A 8/2000 Yeo et al.
6,443,931 B1 * 9/2002 Kurata .................... A61F 13/51 428/198
2003/0050618 A1 3/2003 Kondo et al.
2006/0047257 A1 * 3/2006 Raidel ................... A61F 13/535 604/383
2009/0157032 A1 * 6/2009 MacDonald .......... A61F 13/533 604/379
2010/0280479 A1 * 11/2010 Svensson ............ A61F 13/4752 604/385.23
2014/0171894 A1 * 6/2014 Detani .............. A61F 13/15642 604/374
2016/0206393 A1 * 7/2016 Wang .................... B32B 27/306

FOREIGN PATENT DOCUMENTS

JP 2017516622 A 6/2017
KR 100217832 B1 9/1999
WO 2006101061 A1 9/2006
WO 2015187789 A1 12/2015
WO 2016062590 A1 4/2016

OTHER PUBLICATIONS

Third Written Opinion of PCT/US2018/042676 mailed on Jul. 23, 2019, all enclosed pages cited herein.
International Search Report and Written Opinion of corresponding International Application No. PCT/US2018/042676 mailed Sep. 18, 2018, all enclosed pages cited.
International Preliminary Report on Patentability of PCT/US2018/042676 mailed on Oct. 7, 2019, all enclosed pages cited herein.
Communication pursuant to Article 94(3) EPC issued on corresponding European application No. 18750020.2 on Dec. 3, 2020, all enclosed pages cited herein.
Office Action issued in corresponding Chilean application No. 00154-2020 on Jan. 15, 2021, all enclosed pages cited herein.
First Office Action (with translation) issued in corresponding Chinese Patent Application No. 201880048122.4 on Apr. 13, 2021, all enclosed pages cited.
Communication pursuant to Article 94(3) EPC in corresponding European Patent Application No. 18750020.2 on Jun. 17, 2021, all enclosed pages cited.
Second Office Action (with translation) issued in corresponding Chinese Patent Application No. 201880048122.4 on Oct. 1, 26, 2021, all enclosed pages cited.
Translation of Office Action issued in corresponding Colombian Patent Application No. NC2020/0001337 on Sep. 2, 2022, all enclosed pages cited.
Decision of Refusal (with translation) issued in corresponding Japanese Patent Application No. 2020-502356 on Nov. 8, 2022, all enclosed pages cited.
Office Action (with translation) issued in corresponding Japanese Patent Application No. 2020-502356 on May 24, 1 2022, all enclosed pages cited.
Notice of Final Rejection (with translation) issued in corresponding Korean Patent Application No. 10-2020-7004368 on Jun. 26, 2023, all enclosed pages cited.
Translation of Office Action issued in corresponding Colombian Patent Application No. NC2020/0001337 on Jul. 27, 2023, all enclosed pages cited.
Non-Final Office Action from the corresponding Canadian Application No. 3,070,268, mailed Jul. 31, 2025, all pages cited in its entirety.

* cited by examiner

ABSORBENT COMPOSITES

PRIORITY CLAIM

This application claims priority under 35 U.S.C. § 119(e) to U.S. Provisional Application Ser. No. 62/534,274 filed Jul. 19, 2017, which is expressly incorporated by reference herein in its entirety.

TECHNICAL FIELD

Embodiments of the presently-disclosed invention relate generally to absorbent composites including a nonwoven top layer and an absorbent core layer, in which the absorbent core layer comprises a through-air-bonded nonwoven, such as a high loft nonwoven including continuous and/or staple multi-component fibers (e.g., non-crimped, crimped, and/or thermally-crimpable fibers).

BACKGROUND

Absorbent materials are typically positioned around the fenestration area (e.g., a window through which a surgical procedure may be performed) in a surgical drape. The absorbent material is located around the fenestration area to capture a limited amount of fluid generated during a surgical intervention. These fluids can include body fluids (e.g., blood) and/or fluids used by the surgical team in the performance of their work.

Typically, such absorbent materials comprise cellulosic fibers such as rayon and lyocell in a spunlaced or/and chemical bonded web. Such fabrics have good absorption capacity, however, they suffer from high run off and high absorption time. These two deficiencies indicate that the fabric is slow to take up fluid, which can be detrimental during surgery as it may allow fluid to flow out of the area covered with the absorbent material.

A different group of absorbent materials contain wood pulp to provide absorption. This raw material (e.g., wood pulp), however, has a tendency to form lint in the form of particulates released by the fabric. The creation of lint during a surgical procedure is not desirable.

Another class of absorbent material currently used consists of a three-layer composite including a cover made from a spunbond, a core made from hydrophilic meltblown, and a backing film. This type of fabric, however, exhibits a lower absorption capacity (g/g) while still suffering from high run off.

In yet another class of absorbent materials, a reasonably bulky hydrophilic spunbond is been laminated to a film. Such products, however, also suffers from poor run off (i.e., the % run off is high) and lower absorbency than the cellulosic containing absorbent materials.

Therefore, there remains a need in the art for a cost effective absorbent material, such as for use around a fenestration area on a surgical drape, as a tray cover, or in the healthcare industry for the prevention and/or treatment of skin breakdown in a patient, that has one or more of good abrasion resistance, fast rate of absorption to avoid leakage as characterized by low absorption time, low percentage of run off, and high absorbency.

SUMMARY OF INVENTION

One or more embodiments of the invention may address one or more of the aforementioned problems. Certain embodiments according to the invention provide an absorbent composite including a nonwoven top layer. The nonwoven top layer may comprise a plurality of hydrophilic fibers, in which the fibers may be rendered hydrophilic via topical application of a hydrophilic additive and/or via addition of a hydrophilic additive to the polymer melt used to form at least some (or all) of the fibers forming the nonwoven top layer. The nonwoven top layer may comprise a generally open structure to allow relatively fast penetration by fluids. The absorbent composite may also comprise an absorbent core layer directly or indirectly attached to the nonwoven top layer, in which the absorbent core layer comprises a through-air-bonded nonwoven, such as a high loft nonwoven including continuous and/or staple multi-component fibers (e.g., non-crimped, crimped, and/or thermally-crimpable fibers). Similar to the nonwoven top layer, the absorbent core layer may also comprise a plurality of hydrophilic fibers, in which the fibers may be rendered hydrophilic via topical application of a hydrophilic additive and/or via addition of a hydrophilic additive to the polymer melt used to form at least some (or all) of the fibers forming the absorbent core layer. In accordance with certain embodiments of the invention, the absorbent composite includes (i) a composite-run-off value of less than 50% as determined by ISO 9073-11; (ii) a composite-absorption capacity of at least 600% as determined by ISO 9073; and (iii) a composite-rate of absorption of less than 10 seconds for a 5 ml liquid sample as determined by D824-94. In accordance with certain embodiments of the invention, the absorbent composite may optionally include a film directly or indirectly attached (e.g., bonded) to the absorbent core layer, such that the absorbent core layer is directly or indirectly sandwiched between the nonwoven top layer and the film.

In another aspect, the invention provides a surgical gown, surgical drape, a portion of a surgical drape, or a tray liner comprising an absorbent composite as disclosed herein. In accordance with certain embodiments of the invention, the absorbent composite comprises a fenestration material surrounding a fenestration (e.g., window or aperture) through which a surgical procedure can be performed.

In another aspect, the invention provides a material suitable for use, for example alone or when incorporated into an article of manufacture, in the healthcare industry for the prevention and/or treatment of skin breakdown, which can undesirably lead to complications such as decubitus ulcers. A patient, for example, may experience skin breakdown at or during several points throughout the care of a patient in a hospital, a nursing home, or a homecare setting. In accordance with certain embodiments of the invention, for instance, an absorbent composite either alone or as part of an article of manufacture (e.g., adult diaper, bedding sheet, gown, etc.) that may be placed in contact with the skin of a patient. In this regard, certain embodiments of the invention also provide methods of preventing skin deterioration (e.g., decubitus ulcers) of an individual susceptible to development of skin deterioration (e.g., decubitus ulcers). Individuals to susceptible to development of skin deterioration may include any patient that may spend a considerable amount of time one or a few positions (e.g., a patient that is mostly or wholly confined to a bed) over the course of multiple days. In this regard, absorbent composites in accordance with certain embodiments of the invention may provide a microclimate environment at or adjacent the skin of an individual having one or more of a desirable air permeability, a low coefficient of friction, and/or highly absorbent for proper humidity levels. In another aspect, certain embodiments of the invention also provide methods of treating individuals already suffering or showing signs of skin deterioration (e.g., decubitus ulcers). In this regard, the absorbent composites in accordance with certain embodiments of the invention may provide a micro-climate environment (as noted above) at or adjacent the skin of the individual already suffering or showing signs of skin deterioration (e.g., decubitus ulcers) such that the rate or severity of the skin deterioration may be positively impacted (e.g., rate of deterioration may be slowed, stopped, and/or reversed).

In another aspect, the invention provides a method of making an absorbent composite including the following steps: (i) providing a nonwoven top layer comprising hydrophilic fibers, (ii) providing an absorbent core layer, wherein the absorbent core layer comprises a through-air-bonded nonwoven such as a high loft nonwoven including continuous and/or staple multi-component fibers (e.g., non-crimped, crimped, and/or thermally-crimpable fibers), and (c) directly or indirectly attaching the nonwoven top layer and the absorbent core layer to provide the absorbent composite as disclosed herein. In accordance with certain embodiments of the invention, the method may further comprise topically treating the nonwoven top layer, the absorbent core layer, or both with a hydrophilic additive. Additionally or alternatively, the method may further comprise forming a first polymer melt including a hydrophilic additive and forming the hydrophilic fibers of the nonwoven top layer and/or forming a second polymer melt including a hydrophilic additive and forming absorbent-core-fibers. Methods, in accordance with certain embodiments of the invention, may further comprise attaching a film directly or indirectly to the absorbent core layer, wherein the absorbent core layer is directly or indirectly sandwiched between the nonwoven top layer and the film.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1:
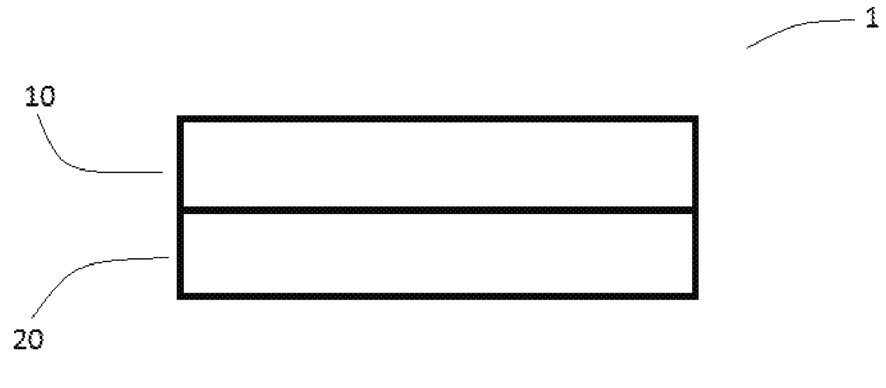
FIG. 1 illustrates an absorbent composite according to one embodiment of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms “a”, “an”, “the”, include plural referents unless the context clearly dictates otherwise.

This invention provides an absorbent composite including a nonwoven top layer, in which the nonwoven top layer may comprise a plurality of hydrophilic fibers (e.g., rendered hydrophilic through the selection of its melt formulation for forming the fibers and/or through topical treatment), and an absorbent core layer directly or indirectly attached to the nonwoven top layer, in which the absorbent core layer comprises a through-air-bonded nonwoven such as a high loft nonwoven including continuous and/or staple multi-component fibers (e.g., non-crimped, crimped, and/or thermally-crimpable fibers). Similar to the nonwoven top layer, the absorbent core layer may also comprise a plurality of hydrophilic fibers (e.g., rendered hydrophilic through the selection of its melt formulation for forming the fibers and/or through topical treatment). In accordance with certain embodiments of the invention, the nonwoven top layer may comprise a pre-bonded spunmelt nonwoven (e.g., spunbond, meltblown, or combinations thereof), such as a point bonded calendered cover, or a carded web made from staple fibers that have been bonded, such as thermally or ultrasonically point bonded. The nonwoven top layer may be attached to the absorbent core layer, which may comprise a through-air-bonded nonwoven, via one or more bonding means, such as by thermal point bonding, ultrasonic bonding (e.g., ultrasonic point bonding), and/or adhesive bonding (e.g., adhesively glued together).

In accordance with certain embodiments of the invention, the nonwoven top layer may provide good hydrophilicity, good openness (e.g., porosity), and good abrasion resistance while the absorbent core layer may provide a high void volume. In accordance with certain embodiments of the invention, the absorbent core layer may comprise continuous and/or staple monocomponent and/or continuous and/or staple multicomponent (e.g., bicomponent) fibers (e.g., non-crimped, crimped, and/or thermally-crimpable fibers). In accordance with certain embodiments of the invention, the absorbent core layer may comprise a blend of continuous and/or staple bicomponent fibers (e.g., non-crimped, crimped, and/or thermally-crimpable fibers) selected to provide resiliency as well as a desirable pore structure as evaluated by air permeability. In accordance with certain embodiments of the invention, the absorbent core layer may comprise a high loft nonwoven comprising continuous (e.g., spunbond filaments), meltblown, and/or staple multicomponent (e.g., bicomponent) fibers that may be crimped and/or thermally-crimpable to impart added loftiness to the absorbent core layer.

The terms “substantial” or “substantially” may encompass the whole amount as specified, according to certain embodiments of the invention, or largely but not the whole amount specified according to other embodiments of the invention.

The terms “polymer” or “polymeric”, as used interchangeably herein, may comprise homopolymers, copolymers, such as, for example, block, graft, random, and alternating copolymers, terpolymers, etc., and blends and modifications thereof. Furthermore, unless otherwise specifically limited, the term “polymer” or “polymeric” shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material. The term “polymer” or “polymeric” shall also include polymers made from various catalyst systems including, without limitation, the Ziegler-Natta catalyst system and the metallocene/single-site catalyst system. The term “polymer” or “polymeric” shall also include, in according to certain embodiments of the invention, polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, air-laid, and bonded carded web processes.

The term "staple fiber", as used herein, may comprise a cut fiber from a filament. In accordance with certain embodiments, any type of filament material may be used to form staple fibers. For example, staple fibers may be formed from cellulosic fibers, polymeric fibers, and/or elastomeric fibers. Examples of materials may comprise cotton, rayon, wool, nylon, polypropylene, and polyethylene terephthalate. The average length of staple fibers may comprise, by way of example only, from about 2 centimeter to about 15 centimeter.

The term "continuous fiber", as used herein, may comprise a filament that has a high length-to-diameter aspect ratio (i.e., length:diameter) such as, for example, exceeding about 500,000:1, exceeding about 750,000:1, or exceeding about 1,000,000:1. In accordance with certain embodiments of the invention, the term "continuous fiber" may comprise a filament that is essentially endless in length.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include a nonwoven described in the literature as SPINLACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "layer", as used herein, may comprise a generally recognizable combination of similar material types and/or functions existing in the X-Y plane.

The term "bicomponent fibers", as used herein, may comprise fibers formed from at least two different polymers extruded from separate extruders but spun together to form one fiber. Bicomponent fibers are also sometimes referred to as conjugate fibers or multicomponent fibers. The polymers are arranged in a substantially constant position in distinct zones across the cross-section of the bicomponent fibers and extend continuously along the length of the bicomponent fibers. The configuration of such a bicomponent fiber may be, for example, a sheath-and-core arrangement wherein one polymer is surrounded by another, or may be a side-by-side arrangement, a pie arrangement, or an "islands-in-the-sea" arrangement, each as is known in the art of multicomponent, including bicomponent, fibers. The "bicomponent fibers" may be thermoplastic fibers that comprise a core fiber made from one polymer that is encased within a thermoplastic sheath made from a different polymer or have a side-by-side arrangement of different thermoplastic fibers. The first polymer often melts at a different, typically lower, temperature than the second polymer. In the sheath/core arrangement, these bicomponent fibers provide thermal bonding due to melting of the sheath polymer, while retaining the desirable strength characteristics of the core polymer. In the side-by-side arrangement, the fibers shrink and crimp creating z-direction expansion.

The term "crimp" or "crimped", as used herein, may comprise a two- or three-dimensional curl or bend such as, for example, a folded or compressed portion having an "L" configuration, a wave portion having a "zig-zag" configuration, or a curl portion such as a helical configuration. In accordance with certain embodiments of the invention, the term "crimp" or "crimped" does not include random two-dimensional waves or undulations in a fiber, such as those associated with normal lay-down of fibers in a melt-spinning process.

The term "high-loft", as used herein, may comprises a material that is compressible by 20% or more when an applied pressure changes from 0.1 kPa to 0.5 kPa according to BS EN ISO 9703-2 (1995). Moreover, "high-loft" nonwovens, as used herein, may comprise a z-direction thickness generally in excess of about 3 mm and a relatively low bulk density. The thickness of a "high-loft" nonwoven layer may be greater than 3 mm (e.g., greater than 4 mm or greater than 5 mm) as determined according to ASTM D573-95, ITS 120.2. "High-loft" nonwovens, as used herein, may additionally have a relatively low density (e.g., bulk density-weight per unit volume), such as less than about 50 $kg/m^3$.

The term "through-air bonded", as used herein, may comprise a nonwoven web consolidated by a bonding process in which hot air is used to fuse the fibers at the surface of the web and optionally internally within the web. By way of example only, hot air can either be blown through the web in a conveyorized oven or sucked through the web as it passes over a porous drum as a vacuum is developed. The temperature of and the rate of hot air are parameters that may determine the level or the extent of bonding in nonwoven web. In accordance with certain embodiments of the invention, the temperature of the hot air may be high enough to melt and/or fuse a first polymeric component (e.g., a sheath component) of a multicomponent fiber (e.g., bicomponent fiber) while not melting a second polymeric component (e.g., a sheath component) of the multicomponent fiber. In accordance with certain embodiments of the invention, the hot air may also initiate crimping of multicomponent fibers (e.g., bicomponent fibers).

All whole number end points disclosed herein that can create a smaller range within a given range disclosed herein are within the scope of certain embodiments of the invention. By way of example, a disclosure of from about 10 to about 15 includes the disclosure of intermediate ranges, for example, of: from about 10 to about 11; from about 10 to about 12; from about 13 to about 15; from about 14 to about 15; etc. Moreover, all single decimal (e.g., numbers reported to the nearest tenth) end points that can create a smaller range within a given range disclosed herein are within the scope of certain embodiments of the invention. By way of example, a disclosure of from about 1.5 to about 2.0 includes the disclosure of intermediate ranges, for example, of: from about 1.5 to about 1.6; from about 1.5 to about 1.7; from about 1.7 to about 1.8; etc.

I. ABSORBENT COMPOSITES AND METHODS OF MAKING THE SAME

In one aspect, the invention provides an absorbent composite including a nonwoven top layer. The nonwoven top layer may comprise a plurality of hydrophilic fibers, in which the fibers may be rendered hydrophilic via topical application of a hydrophilic additive and/or via addition of a hydrophilic additive to the polymer melt used to form at least some (or all) of the fibers forming the nonwoven top layer. The nonwoven top layer may comprise a generally open structure to allow relatively fast penetration by fluids. The absorbent composite may also comprise an absorbent core layer directly or indirectly attached to the nonwoven top layer, in which the absorbent core layer comprises a through-air-bonded nonwoven. Similar to the nonwoven top layer, the absorbent core layer may also comprise a plurality of hydrophilic fibers, in which the fibers may be rendered hydrophilic via topical application of a hydrophilic additive and/or via addition of a hydrophilic additive to the polymer melt used to form at least some (or all) of the fibers forming the absorbent core layer. In accordance with certain embodiments of the invention, the absorbent composite includes (i) a composite-run-off value of less than 50% as determined by ISO 9073-11; (ii) a composite-absorption capacity of at least 600% as determined by ISO 9073; and (iii) a composite-rate of absorption of less than 10 seconds for a 5 ml liquid sample as determined by D824-94. In accordance with certain embodiments of the invention, the absorbent composite may optionally include a film directly or indirectly attached (e.g., bonded) to the absorbent core layer, such that the absorbent core layer is directly or indirectly sandwiched between the nonwoven top layer and the film.

Figure 2:
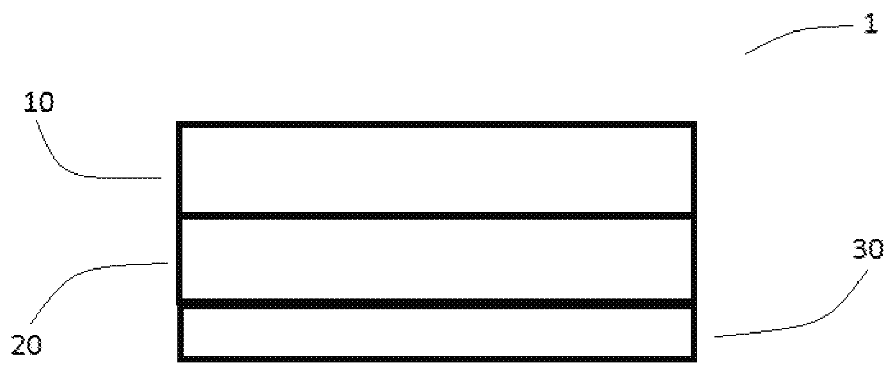
FIG. 2 illustrates an absorbent composite including a film according to one embodiment of the invention.

FIG. 1, for instance, illustrates an absorbent composite according to certain embodiments of the invention. The absorbent composite 1 illustrated in FIG. 1 includes a nonwoven top layer 10 bonded to an absorbent core layer 20. FIG. 2 illustrates an absorbent composite including a film in accordance with certain embodiments of the invention. For instance, the absorbent composite 1 illustrated in FIG. 2 includes a nonwoven top layer 10 bonded to an absorbent core layer 20 and a film 30 bonded to the absorbent core layer 20, in which the absorbent core layer is sandwiched between the nonwoven top layer and the film.

In accordance with certain embodiments of the invention, the nonwoven top layer may comprise a spunmelt nonwoven, such as a spunbond nonwoven, meltblown nonwoven, or a combination thereof. For example, the nonwoven top layer may comprise one or more meltblown layer and one or more spunbond layers. In accordance with certain embodiments of the invention, the nonwoven top layer may comprise a $S1_a$-$M_b$-$S2_c$ structure; wherein 'S1' is a first spunbond material, 'M' is a meltblown material, 'S2' is a second spunbond material, and 'a', 'b', and 'c' indicate the number of respective layers and each may independently be selected from a value of at least 1, such as 1, 2, 3, 4, or 5. In accordance with certain embodiments of the invention, the nonwoven top layer may comprise, additionally or alternatively to a spunmelt nonwoven, a carded web comprising staple fibers, such as a point bonded carded web.

The nonwoven top layer, in accordance with certain embodiments of the invention, may comprise at least about 30% by weight of hydrophilic fibers, such as at least about 40%, at least about 50%, at least about 60%, at least about 70%, at least about 80%, at least about 90%, or about 100% by weight of hydrophilic fibers. In accordance with certain embodiments of the invention, for instance, the nonwoven top layer may comprise at most about any of the following: 100%, 95%, 90%, 80%, 70%, 60%, 50%, and 40% by weight of hydrophilic fibers and/or at least about any of the following: 20%, 25%, 30%, 35%, 40%, 50%, 60%, 70%, 80%, and 90% by weight of hydrophilic fibers.

In accordance with certain embodiments of the invention, the nonwoven top layer my comprise a generally "open" structure that facilitates the penetration of fluid through the nonwoven top layer. The "openness" of the nonwoven top layer may be evaluated by air permeability of the nonwoven top layer, in which a lower air permeability may be indicative a more closed structure and a higher air permeability may be indicative of a relatively more "open" structure. In accordance with certain embodiments of the invention, for example, the nonwoven top layer may include an air permeability of at least about 100 cubic-feet-per-minute (CFM) as determined by IST 70.1, such as at least about 150 CFM, at least about 200 CFM, at least about 250 CFM, at least about 300 CFM, at least about 350 CFM, at least about 400 CFM, or at least about 500 CFM as determined by IST 70.1. In accordance with certain embodiments of the invention, for instance, the nonwoven top layer may include an air permeability of at most about any of the following: 700, 600, 500, 400, 350, 300, and 250 CFM as determined by IST 70.1 and/or at least about any of the following: 40, 50, 75, 100, 125, 150, 175, 200, 225, and 250 CFM as determined by IST 70.1.

The nonwoven top layer, in accordance with certain embodiments of the invention, may comprise a pre-bonded nonwoven including a bonding area. For instance, the nonwoven top layer may comprise a bonding area prior to formation of the absorbent composite comprising from about 1-30% of the surface of the nonwoven top layer, such as from about 1-25%, from about 3-20%, or from about 5-15%. In accordance with certain embodiments of the invention, for instance, the nonwoven top layer may comprise a bonding area prior to formation of the absorbent composite comprising at most about any of the following: 30%, 25%, 20%, 15%, 10%, and 5% of the surface of the nonwoven top layer and/or at least about any of the following: 1%, 3%, 5%, 8%, 10%, 12%, 15%, 18%, and 20% of the surface of the nonwoven top layer. In this regard, the nonwoven top layer may include a bonding pattern prior to formation of the absorbent composite comprising, for example, thermally-formed point bonds, ultrasonic bonds, mechanical bonds, or any combination thereof.

In accordance with certain embodiments of the invention, the nonwoven top layer comprises a desirable resistance to abrasion, which mitigates the formation of lint when in use. Absorbent composites including the nonwoven top layer may be tested for abrasion resistance, in which the nonwoven top layer is directly subjected to the test (i.e., IST 20.5) and comprises a top-layer-Martindale Abrasion value of less than about 2 mg as determined by IST 20.5, such as less than about 1.75 mg, less than about 1.5 mg, less than about 1.25 mg, less than about 1.0 mg, less than about 0.75 mg, or less than about 0.50 mg as determined by IST 20.5. In accordance with certain embodiments of the invention, for instance, the top-layer-Martindale Abrasion value of at most about any of the following: 3, 2.5, 2, 1.5, 1, 0.75, and 0.5 mg as determined by IST 20.5 and/or at least about any of the following: 0.25, 0.50, 0.75, 1.0, and 1.25 mg as determined by IST 20.5. In accordance with certain embodiments of the invention, the absorbent composites including the nonwoven top layer may be tested in which the nonwoven top layer is directly tested and comprises a top-layer-abrasion cycle value of at most about any of the following: 7000, 6000, 5750, 5500, 5250, and 5000 cycles as determined by ASTM D4966 and/or at least about any of the following: 3000, 3500, 4000, 4500, and 5000 as determined by ASTM D4966.

The nonwoven top layer, in accordance with certain embodiments of the invention, may comprises a basis weight from about 10-60 grams-per-square-meter (gsm), such as from about 15-50 gsm, 20-50 gsm, 25-45 gsm, 25-40 gsm, or from about 25-35 gsm. For instance, the nonwoven top layer may comprise a basis weight of at most about any of the following: 70, 60, 50, 40, 30, 20, and 15 gsm and/or at least about any of the following: 5, 10, 12, 15, 20, 25, and 30 gsm.

As noted above, the nonwoven top layer may comprise a plurality of hydrophilic fibers. Such fibers may be rendered hydrophilic via topical application or treatment with a hydrophilic additive and/or a hydrophilic additive may be incorporated into the polymer melt used to form the plurality of hydrophilic fibers used, at least in part, for formation of the nonwoven top layer. In this regard, the plurality of hydrophilic fibers of the nonwoven top layer may comprise monocomponent fibers, multicomponent fibers, or a combination thereof. In accordance with certain embodiments of the invention, the hydrophilic fibers of the nonwoven top layer include monocomponent fibers comprising one or more synthetic polymers, such as a polyolefins, polyesters, polyamides, polylactic acid, polyglycolic acid, or any combination thereof. Examples of suitable polyolefins includes, for example, a polypropylene, a polyethylene, copolymers thereof, or blends thereof. As noted above, these fibers may be rendered hydrophilic to facilitate intake of liquids, such as water and blood. In accordance with certain embodiments of the invention, the hydrophilic fibers of the nonwoven top layer include multicomponent fibers, such as bicomponent fibers including a sheath-and-core configuration and/or a side-by-side configuration. In accordance with certain embodiments of the invention, the nonwoven top layer comprises hydrophilic bicomponent fibers, such as bicomponent fibers including a sheath comprising a polyolefin (e.g., a polyethylene) and a core comprising at least one of a polyolefin (e.g., a polypropylene) or a polyester.

In accordance with certain embodiments of the invention, the absorbent core layer may comprises a plurality of absorbent-core-fibers, in which the plurality of absorbent-core-fibers may comprise continuous fibers (e.g., spunbond filaments), meltblown fibers, staple fibers, or combinations thereof. For example, the absorbent core layer according to certain embodiments of the invention may comprise a carded nonwoven comprising staple fibers, a nonwoven comprising continuous fibers (e.g., spunbond filaments) alone or in combination with meltblown fibers and/or staple fibers. In accordance with certain embodiments of the invention, the absorbent-core-fibers (e.g., continuous, meltblown, and/or staple fibers) may comprise monocomponent and/or multicomponent (e.g., bicomponent) fibers (e.g., non-crimped, crimped, and/or thermally-crimpable fibers). In accordance with certain embodiments of the invention, the absorbent core layer may comprise a high loft nonwoven comprising continuous (e.g., spunbond filaments), meltblown, and/or staple multicomponent (e.g., bicomponent) fibers that may be crimped and/or thermally-crimpable to impart added loftiness to the absorbent core layer. The plurality of absorbent-core-fibers, for example, may comprise a plurality of hydrophilic fibers. For example, the absorbent-core-fibers may comprise at least about 30% by weight of hydrophilic fibers, such as at least about 40%, at least about 50%, at least about 60%, at least about 70%, at least about 80%, at least about 90%, or about 100% by weight of hydrophilic fibers. In accordance with certain embodiments of the invention, for instance, the absorbent core layer may comprise at most about any of the following: 100%, 95%, 90%, 80%, 70%, 60%, 50%, and 40% by weight of hydrophilic fibers and/or at least about any of the following: 20%, 25%, 30%, 35%, 40%, 50%, 60%, 70%, 80%, and 90% by weight of hydrophilic fibers. In accordance with certain embodiments of the invention, the absorbent core layer is devoid of natural cellulosic materials and synthetic cellulosic materials. In accordance with certain alternative embodiments of the invention, the absorbent core may comprise natural cellulosic materials and/or synthetic cellulosic materials.

The absorbent-core-fibers, for example, may include monocomponent fibers comprising one or more synthetic polymers, such as a polyolefin, a polyester, a polyamide, polylactic acid, polyglycolic acid, or any combination thereof. Suitable polyolefins, in accordance with certain embodiments of the invention, may comprise a polypropylene, polyethylene, copolymers thereof, or blends thereof. As noted above, these fibers may be rendered hydrophilic to facilitate intake and/or holding of liquids, such as water and blood. In accordance with certain embodiments of the invention, the hydrophilic fibers of the absorbent core layer may include multicomponent fibers (e.g., continuous filaments, meltblown fibers, and/or staple fibers), such as bicomponent fibers including, for example, a sheath-and-core configuration and/or a side-by-side configuration. In accordance with certain embodiments of the invention, the absorbent core layer comprises hydrophilic continuous, meltblown, and/or staple bicomponent fibers, such as bicomponent fibers including a sheath comprising a polyolefin (e.g., a polyethylene) and a core comprising at least one of a polyolefin (e.g., a polypropylene) or a polyester. In accordance with certain embodiments of the invention, the absorbent core layer may comprise a high loft nonwoven comprising continuous (e.g., spunbond filaments), meltblown, and/or staple multicomponent (e.g., bicomponent) fibers that may be crimped and/or thermally-crimpable to impart added loftiness to the absorbent core layer. In accordance with certain embodiments of the invention, the absorbent-core-fibers may comprise a blend of monocomponent fibers and multicomponent fibers. In accordance with certain other embodiments of the invention, the absorbent-core-fibers consist of bicomponent fibers, such as bicomponent continuous fibers (e.g., spunbond filaments), meltblown fibers, and/or staple fibers.

In accordance with certain embodiments of the invention, the absorbent-core-fibers may have an average denier of at most about 5 denier, such as at most about 4, 3, 2.5, 2, or 1.5 denier. In accordance with certain embodiments of the invention, for example, the absorbent-core-fibers may have an average denier of at most about any of the following: 6, 5.5, 5, 4.5, 4, 3.5, and 3 denier and/or at least about any of the following: 1, 1.5, 1.75, 2.0, 2.5, 3.0, and 3.5 denier.

In accordance with certain embodiments of the invention, the absorbent-core-fibers may have at least about 50% by weight a denier from about 1 to about 3 denier, such as at least about 70%, at least about 85%, at least about 90%, or about 100% by weight of the absorbent-core-fibers have a denier that is from 1 to 3 denier. In accordance with certain embodiments of the invention, for example, the absorbentcore-fibers may comprise at most about any of the following: 100%, 90%, 85%, 80%, 70%, 60%, and 50% by weight a denier from about 1 to about 3 denier and/or at least about any of the following: 25%, 35%, 40%, 45%, 50%, 55%, 60%, and 70% by weight a denier from about 1 to about 3 denier. In accordance with certain embodiments of the invention, the absorbent-core-fibers may comprise a blend of (i) fine fibers, for example, having a denier from about 1 to about 3 denier, and (ii) course fibers having, for example, a denier from about 6 to about 9 denier.

The absorbent core layer, in accordance with certain embodiments of the invention, may comprise a blend of (i) a first group of bicomponent fibers having a polyethylene sheath and a polypropylene core, and (ii) a second group of bicomponent fibers having a polyethylene sheath and a polyester core. In accordance with certain embodiments of the invention, a ratio of the first group of bicomponent fibers to the second group of bicomponent fibers, based on weight, may comprises from about 10:90 to about 70:30, such as from about 20:80 to about 60:40, from about 20:80 to about 50:50, or from about 20:80 to about 40:60.

In accordance with certain embodiments, the absorbent core layer comprises a relatively high void volume that facilitates penetration of liquid into the absorbent core layer and the ability to retain the fluid in the pores of the absorbent core layer. In accordance with certain embodiments of the invention, the absorbent core layer comprises a void volume greater than 12 cc/g, such as greater than about 14 cc/g, greater than about 15 cc/g, greater than about 16 cc/g, greater than about 17 cc/g, greater than about 18 cc/g, greater than about 19 cc/g, or greater than about 20 cc/g. In accordance with certain embodiments of the invention, for example, the absorbent core layer may comprise a void volume of at most about any of the following: 30, 25, 20, 19, 18, 17, 16, and 15 cc/g and/or at least about any of the following: 10, 12, 15, 18, and 20 g/cc.

The absorbent core layer, in accordance with certain embodiments of the invention, may comprise an absorbent-core-layer-air permeability below about 1600 CFM as determined by IST 70.1, such as about below about 1500 CFM, 1400 CFM, 1300 CFM, 1200 CFM, 1100 CFM, 1000 CFM, 900 CFM, 800 CFM, and 700 CFM. In accordance with certain embodiments of the invention, for example, the absorbent core layer may comprise an absorbent-core-layer-air permeability of at most about any of the following: 1600, 1500, 1400, 1300, 1200, 1100, 1000, and 900 CFM as determined by IST 70.1 and/or at least about any of the following: 50, 100, 200, 300, 400, 500, 600, 700, 800, and 900 as determined by IST 70.1.

The absorbent core layer, in accordance with certain embodiments of the invention, may comprise an absorbent-core-layer-absorption capacity that is greater than about 1200% as determined by ISO 9073, such as about greater than 1400%, 1600%, 1800%, 2000%, 2200%, 2400%, 2600%, 2800%, or 3000% as determined by ISO 9073. In accordance with certain embodiments of the invention, for example, the absorbent core layer may comprise an absorbent-core-layer-absorption capacity of at most about any of the following: 1600, 1500, 1400, 1300, 1200, 1100, 1000, and 900 CFM as determined by IST 70.1 and/or at least about any of the following: 50, 100, 200, 300, 400, 500, 600, 700, 800, and 900 as determined by IST 70.1.

In accordance with certain embodiments of the invention, the absorbent core layer may comprise an absorbent-core-layer-basis weight from about 10-200 gsm, such as from about 10-175 gsm, from about 10-150 gsm, from about 10-125 gsm, from about 10-100 gsm, from about 10-75 gsm, from about 10-50 gsm, from about 10-50 gsm, from about 10-25 gsm, or from about 15-25 gsm. For instance, the absorbent-core-layer-basis weight may comprise at most about any of the following: 200, 175, 150, 125, 100, 75, and 50 gsm and/or at least about any of the following: 5, 10, 15, 20, 25, 35, 45, 50, and 60 gsm.

In accordance with certain embodiments of the invention, the nonwoven top layer and the absorbent core layer are directly or indirectly bonded together via a composite-bonding pattern formed from thermally-formed point bonds, ultrasonic bonds, mechanical bonds, adhesive (e.g., binder or glue) bonds, or any combination thereof. The composite-bonding pattern, in accordance with certain embodiments of the invention, may comprise a plurality of ultrasonic point bonds.

The composite-bonding pattern, in accordance with certain embodiments of the invention, may define a composite-bonding area of no more than 30% of a surface of the absorbent composite, such as no more than about 25%, no more than about 20%, no more than about 15%, no more than about 10%, no more than about 5%, or no more than about 3% of a surface of the absorbent composite. In accordance with certain embodiments of the invention, for instance, the composite-bonding area may comprise at most about any of the following: 30%, 25%, 20%, 15%, 10%, 5%, and 3% of the surface of the absorbent composite and/or at least about any of the following: 0.5%, 1%, 2%, 3%, 5%, 8%, 10%, 12%, and 15% of the surface of the absorbent composite.

In accordance with certain embodiments of the invention, the absorbent composite may further comprise a film attached to the absorbent core layer, wherein the absorbent core layer is directly or indirectly sandwiched between the nonwoven top layer and the film. The film, in accordance with certain embodiments of the invention, may comprise a water impermeable film and may comprise at least one polyolefin, such as a polyethylene. The film, for example, may be directly or indirectly attached to the absorbent core layer via an adhesive layer disposed directly or indirectly between the absorbent core layer and the film. In other embodiments in accordance with the invention, the film is extrusion coated directly or indirectly onto the absorbent core layer.

As noted above, certain embodiments of the invention comprise one or more desirable properties for an absorbent composite suitable for a variety of uses. For example, the absorbent composite may comprise a composite-run-off value of less than 45% as determined by ISO 9073-11, such as less than 45%, less than 40%; less than 35%, less than 30%, less than 30%, less than 25%, or less than 20% as determined by ISO 9073-11. In accordance with certain embodiments of the invention, for instance, absorbent composite may comprise a composite-run-off value at most about any of the following: 60%, 55%, 50%, 40%, 35%, 30%, 25%, and 20% as determined by ISO 9073-11 and/or at least about any of the following: 5%, 10%, 12%, 15%, 20%, and 25% as determined by ISO 9073-11.

The absorbent composite, in accordance with certain embodiments of the invention, may comprise a composite-absorption capacity of at least 600% as determined by ISO 9073, such as at least 650%, at least 700%, at least 725%, at least 750%, at least 775%, at least 800%, at least 825%, at least 850%, at least 875%, at least 900%, at least 950%, at least 1000%, or at least about 1500% as determined by ISO 9073. In accordance with certain embodiments of the invention, for instance, absorbent composite may comprise a composite-absorption capacity at most about any of the following: 1500%, 1400%, 1300%, 1200%, 1100%, 1000%, 950%, 900%, 875%, 850%, 825%, and 800% as determined by ISO 9073 and/or at least about any of the following: 500%, 550%, 600%, 700%, and 725% as determined by ISO 9073.

In accordance with certain embodiments of the invention, the absorbent composite comprises a composite-rate of absorption of less than 9 seconds for a 5 ml liquid sample as determined by D824-94, such as less than 8 second, less than 7 second, less than 6 second, less than 5 second, or less than 4 second as determined by D824-94. In accordance with certain embodiments of the invention, for instance, absorbent composite may comprise a composite-rate of absorption at most about any of the following: 12, 10, 9, 8, 7, and 6 seconds as determined by D824-94 and/or at least about any of the following: 4, 5, 6, 7, and 8 second as determined by D824-94.

The absorbent composite, in accordance with certain embodiments of the invention, may comprise a composite-void volume of at least 7 g/cc, such as at least 8 cc/g, or at least 9 cc/g. In accordance with certain embodiments of the invention, for instance, absorbent composite may comprise a composite-void volume at most about any of the following: 12, 10, 9, and 8 cc/g and/or at least about any of the following: 1, 2, 3, 4, 5, 6, and 7 cc/g.

The absorbent composite, in accordance with certain embodiments of the invention, may comprise a composite-Martindale Abrasion value of less than about 2 mg as determined by IST 20.5, such as less than about 1.75 mg, less than about 1.5 mg, less than about 1.25 mg, less than about 1.0 mg, less than about 0.75 mg, or less than about 0.50 mg as determined by IST 20.5. In accordance with certain embodiments of the invention, for instance, the absorbent composite may include a composite-Martindale Abrasion value of at most about any of the following: 3, 2.5, 2, 1.5, 1, 0.75, and 0.5 mg as determined by IST 20.5 and/or at least about any of the following: 0.25, 0.50, 0.75, 1.0, and 1.25 mg as determined by IST 20.5. In accordance with certain embodiments of the invention, the absorbent composite may comprise a composite-abrasion cycle value of at most about any of the following: 7000, 6000, 5750, 5500, 5250, and 5000 cycles as determined by ASTM D4966 and/or at least about any of the following: 3000, 3500, 4000, 4500, and 5000 as determined by ASTM D4966.

The absorbent composite, in accordance with certain embodiments of the invention, may comprise a composite-water-absorption ratio between the weight of water absorbed by the absorbent composite to the dry weight of the composite from 6:1 to 15:1 as determined by ISO 9073, such as from 6:1 to 12:1, from about 7:1 to 10:1, from about 7:1 to 9:1, from about 7:1 to 8.5:1, or from 7.5:1 to 8.5:1.

Figure 3:
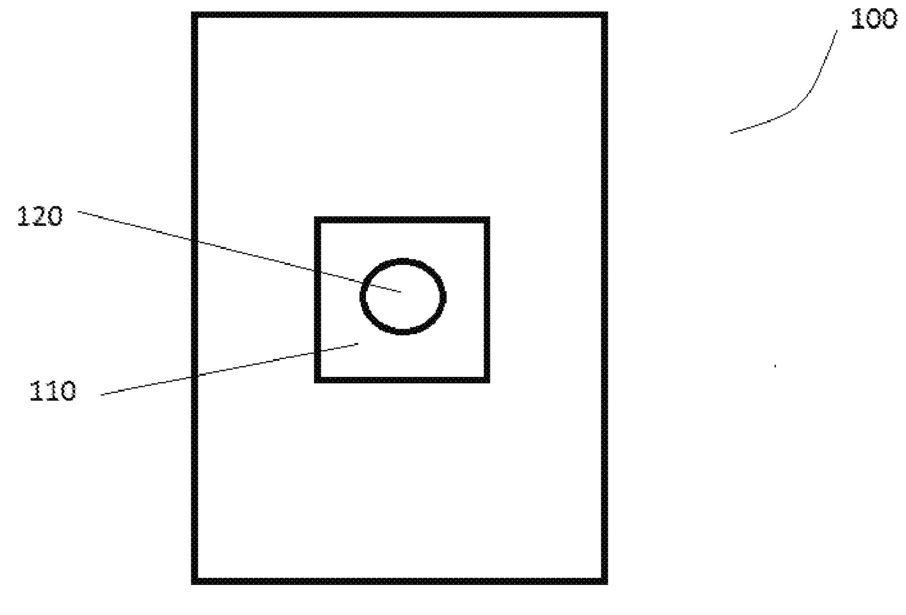
FIG. 3 illustrates a surgical drape including an absorbent composite disposed around a fenestration.

As noted above, absorbent composites in accordance with certain embodiments of the invention may comprise a combination of properties suitable for a variety of applications in which rapid liquid absorption, absorption capacity, and/or limited run-off while maintaining desirable resistance to abrasion. In accordance with certain embodiments of the invention, for example, the absorbent composite (as disclosed herein) may be provided in the form of a surgical drape, a portion of a surgical drape, a tray liner, or an under-patient absorbent pad. In accordance with certain embodiments of the invention, the absorbent composite comprises a fenestration material surrounding a fenestration through which a surgical procedure can be performed. For example, FIG. 3 illustrates a surgical drape 100 including an absorbent composite 110 disposed around a fenestration 120 through with a medical (e.g., surgical) procedure may be performed.

In another aspect, the invention provides a material suitable for use, for example alone or when incorporated into an article of manufacture, in the healthcare industry for the prevention and/or treatment of skin breakdown, which can undesirably lead to complications such as decubitus ulcers. A patient, for example, may experience skin breakdown at or during several points throughout the care of a patient in a hospital, a nursing home, or a homecare setting. In accordance with certain embodiments of the invention, for instance, an absorbent composite either alone or as part of an article of manufacture (e.g., adult diaper, bedding sheet, gown, liners, underpads, surgical underlays, etc.) that may be placed in contact with the skin of a patient. By way of example only, the absorbent core may comprise staple bicomponent fibers and/or continuous bicomponent fibers (e.g., spunbond filaments) having a side-by-side arrangement and/or a sheath-and-core arrangement. Certain embodiments of the invention also provide methods of preventing skin deterioration (e.g., decubitus ulcers) of an individual susceptible to development of skin deterioration (e.g., decubitus ulcers). Individuals to susceptible to development of skin deterioration may include any patient that may spend a considerable amount of time one or a few positions (e.g., a patient that is mostly or wholly confined to a bed) over the course of multiple days. In this regard, absorbent composites in accordance with certain embodiments of the invention may provide a micro-climate environment at or adjacent the skin of an individual having one or more of a desirable air permeability, a low coefficient of friction, and/or highly absorbent for proper humidity levels. In another aspect, certain embodiments of the invention also provide methods of treating individuals already suffering or showing signs of skin deterioration (e.g., decubitus ulcers). In this regard, the absorbent composites in accordance with certain embodiments of the invention may provide a micro-climate environment (as noted above) at or adjacent the skin of the individual already suffering or showing signs of skin deterioration (e.g., decubitus ulcers) such that the rate or severity of the skin deterioration may be positively impacted (e.g., rate of deterioration may be slowed, stopped, and/or reversed.

In another aspect, the invention provides a method of making an absorbent composite including the following steps: (i) providing a nonwoven top layer comprising hydrophilic fibers, (ii) providing an absorbent core layer, wherein the absorbent core layer comprises a through-air-bonded nonwoven, and (c) directly or indirectly attaching the nonwoven top layer and the absorbent core layer to provide the absorbent composite as disclosed herein. In accordance with certain embodiments of the invention, the method may further comprise topically treating the nonwoven top layer, the absorbent core layer, or both with a hydrophilic additive. Additionally or alternatively, the method may further comprise forming a first polymer melt including a hydrophilic additive and forming the hydrophilic fibers of the nonwoven top layer and/or forming a second polymer melt including a hydrophilic additive and forming absorbent-core-fibers. Methods, in accordance with certain embodiments of the invention, may further comprise attaching a film directly or indirectly to the absorbent core layer, wherein the absorbent core layer is directly or indirectly sandwiched between the nonwoven top layer and the film. In accordance with certain embodiments of the invention, the step of attaching the film to the absorbent core layer may comprise adhesively laminating the film to the absorbent core layer, for example via a continuous or discontinuous layer of adhesive (e.g., a pressure-sensitive adhesive). In accordance with certain other embodiments of the invention, the step of attaching the film to the absorbent core layer may comprise extrusion coating the film onto the absorbent core layer.

II. EXAMPLES

The present disclosure is further illustrated by the following examples, which in no way should be construed as being limiting. That is, the specific features described in the following examples are merely illustrative and not limiting.

Test Methods

Absorption capacity has been measured as per ISO 9073 test method and expressed in percentage (%) that represent the weight of liquid absorbed relative to the weight of the dry sample.

Water Absorbed Per Square Centimeter is determined by test method ISO 9073, in which the weight of water absorbed in grams is divided by the area (expressed in a square centimeter) of the sample tested.

Water Absorbed Per Gram of Material is determined by dividing the absorption capacity (as determined by ISO 9073) by 100.

Rate of Absorption is the rate of absorption as determined per ASTM method D824-94 where the liquid used is deionized water. The composite is used as the sample being tested and the volume of dispensed liquid is 1 ml for a fist set of tests and 5 ml for a second set of tests.

Void Volume (VO) is the amount of void space in the nonwoven fabric expressed as cubic centimeters per gram of sample. Void volume is calculated from the measurement of the thickness, the basis weight of the sample, and the density of the material forming the sample. For polypropylene a density of 0.905 g per cubic centimeter is used while for polyethylene a density of 0.95 g per cubic centimeter is used. For PET, a density of 1.38 g per cubic centimeter is used. For nonwovens made of bicomponent fibers, the density was calculated using the density of each polymer weighted by the fraction of the fiber they represented. This is illustrated by the following equation where a polymer #1 (P1) has a density (D1) in g/cc and constitutes the fraction (F1) of the fiber and a polymer #2 (P2) has the density (D2) and constitutes the fraction (F2) of the fiber. The sum of the fractions is equal to 1.

For the samples (e.g., composite) the void volume was calculated from the bulk of the sample and the density of the solid material, the latter having being calculated from density of the material in each layer weighted by the percentage of the total weight represented by that layer.

$$\text{Density of the bicomponent fiber } (DF)\text{: } DF=(D1*F1)+(D2*F2)$$

The equation for calculating void volume (VO) can be expressed as follows:

$$VO=(V1-V2)/BW;$$

where, V1 is the volume for one (1) square meter of the sample being measured in cubic centimeters, and is calculated from the thickness measurement T1 as follows:

$$V1=10{,}000*T1,$$

where T1 is the sample thickness expressed in cm and measured as per ASTM D5729, where V2 is the volume occupied by the solid material in one (1) square meter (e.g. for a nonwoven this volume consisted of the volume occupied by the fibers) and can be calculated using the following formula:

$$V2=BW/DF;$$

where BW is the basis weight of the sample in gram per square meter and DF is the density of the polymer or polymer blend used to make the sample and is expressed in gram per cubic centimeter.

Comparative Example 1

Comparative Example 1 was a 68 gsm composite made from a commercially available SMMMS nonwoven treated with a hydrophilic surfactant that was glue laminated to a 20 gsm green colored film. The SMMMS nonwoven identified as SB1 was a spunmelt nonwoven made by Berry Global under the code PD02032017. This polypropylene based nonwoven had a total basis weight of 45 gsm and was made from two outer layers of continuous filaments (S) that account for about 77% of the nonwoven by weight and three inner layers of meltblown (M) that account for 23% of the nonwoven by weight. These layers forming the nonwoven were in-line bonded by calendering using a bonding pattern that had a 15.5% bonding area. This nonwoven had been topically treated with a surfactant to make it wettable and absorbent. This nonwoven was laminated to a film using 3 gsm of pressure sensitive glue that was sprayed on the film prior to be nipped against the nonwoven. The film had a basis weight of about 20 gsm and was made from a blend of LLDPE, LDPE and a green color masterbatch.

Example 1

Example 1 was a composite that was made by first ultrasonic bonding (i) a spunbond forming the nonwoven top layer, and (ii) a through-air-bonded nonwoven forming the absorbent core layer. This ultrasonic-bonded composite was then glued to a film backing. The spunbond forming the nonwoven top layer (SB2) was a 30 gsm spunbond made of polypropylene using a 2-beam Reicofil 2 spunbond production line and was thermally bonded by calendering this web with a pattern that produced a bonding area that covered about 16.5% of the fabric. The through-air-bonded carded web (TAB1) forming the absorbent core layer had a basis weight of 22 gsm and was formed from a 50/50 blend of 1.5 and 2 denier bicomponent fibers, in which these fibers are of the sheath/core configuration with the core being made of polyester while the sheath is made from polyethylene. TAB1 was made by first blending the fibers, carding them into a web, and then bonding this web using a through-air bonding oven. The fibers used for TAB1 were crimped staple fibers that had a length of 38 mm and were treated with a hydrophilic finish. The top layer (SB2) and the through-air bonded core (TAB1) were ultrasonic bonded together using a pin bonding pattern producing a bonding area of about 1%. The film had a basis weight of 16 gsm and was made from a blend of LLDPE and LDPE. The glue lamination was achieved by spraying the film with 3 gsm of pressure sensitive glue and nipping it to the nonwoven composite.

Example 2

The composite of Example 2 was made the same way as described in Example 1 except that the through-air-bonded absorbent core layer (TAB2) had a basis weight of 24 gsm and was made from a 30/70 blend of 1.5 denier PE/PP (i.e., polyethylene sheath and polypropylene core) and 2 denier PE/PET (i.e., polyethylene sheath and polyester core) bicomponent fibers, in which the sheath component for all fibers was made from polyethylene.

Example 3

The composite of Example 3 was made by forming the same ultrasonic bonded composite comprising SB2 and TAB1 as described in Example 1 and then extrusion coating the through-air-bonded side of this composite with a 20 gsm polyethylene film made from a blend of three different grades of polyethylene.

Example 4

To evaluate the use of continuous bicomponent filaments for the formation of an absorbent core layer, a through-air-bonded nonwoven formed from continuous bicomponent filaments (TAB3) was formed and had a basis weight of 22.4 gsm. The continuous bicomponent filaments were formed on a Reicofil spunbond production line and had a side-by-side arrangement, in which a first side of the filaments comprised a polyester and a second side of the filaments comprises a polyethylene. The web of continuous bicomponent filaments was treated with a hydrophilic finish and consolidated (e.g., bonded) using a through-air bonding oven.

Table 1 summarizes the properties of the individual layers from Examples 1-4. Table 2 summarizes the result of Comparative Example 1 and Examples 1-3.

TABLE 1

| | Nominal Basis weight gsm | ISO 9073-6 Absorption Capacity % | ASTM D5729 Bulk cm | Bulk:B.Wt Ratio cm/gsm | ISO 9073 Water Absorbed/ $cm^2$ $g/cm^2$ | D824-94 Rate of Absorption (1 ml) sec | D824-94 Rate of Absorption (5 ml) sec | IST 70.1 Air Permeability cfm | Void Volume (VO) cc/g |
|---|---|---|---|---|---|---|---|---|---|
| TAB1 | 22 | 2870 | 0.045 | 0.002 | 0.067 | 4.3 | 3.4 | 1130 | 19.6 |
| TAB2 | 24 | 2526 | 0.049 | 0.002 | 0.06 | 4.2 | 3.7 | 974 | 19.5 |
| TAB3 | 22.4 | 1775 | 0.033 | 0.0015 | 0.039 | 5.23 | — | — | 13.6 |
| SB1 | 45 | 837 | 0.039 | 0.0009 | 0.037 | 10.3 | 26 | 46 | 7.6 |
| SB2 | 30 | 727 | 0.028 | 0.0009 | 0.022 | 26.2 | 101.7 | 382 | 8.2 |

TABLE 2

| | ASTM D3776 Composite Basis Weight $g/m^2$ | ASTM D3776 Film Basis Weight $g/m^2$ | ASTM D3776 Absorbent Material Estimated Basis Weight $g/m^2$ | ASTM D5729 Bulk cm | Bulk: B.Wt. Ratio cm/gsm | Composite Void Volume (VO) cc/g | D824-94 Rate of Absorption (1 ml) sec | D824-94 Rate of Absorption (5 ml) sec | ISO 9073 Absorption Capacity % |
|---|---|---|---|---|---|---|---|---|---|
| Comparative Example 1 | 67.8 | 19.2 | 45.6 | 0.044 | 0.0006 | 5.4 | 6.7 | 21.5 | 574 |
| Inventive example 1 | 71.5 | 16.2 | 52.3 | 0.071 | 0.0010 | 8.9 | 4.0 | 4.1 | 852 |
| Inventive example 2 | 73.5 | 16.7 | 53.8 | 0.070 | 0.0010 | 8.5 | 4.3 | 5.5 | 759 |
| Inventive example 3 | 72.3 | 20.0 | 52.3 | 0.064 | 0.0009 | 7.8 | 4.0 | 5.4 | 730 |

| | ISO 9073 Water Absorbed/ square cm $g/cm^2$ | ISO 9073 Weight of Water Absorbed/ Dry Weight of Composite g/g | ISO-9073-11 Run Off % | IST 20.5 Martindale Abrasion (abs side) mg | ASTM D4966 Martindale Abrasion (abs side) cycles | EN 29073-3 Dry MD Tensile Strip N/5 cm | EN 29073-3 Dry CD Tensile Strip N/5 cm |
|---|---|---|---|---|---|---|---|
| Comparative Example 1 | 0.039 | 5.7 | 67 | 0.73 | 3667 | 97 | 46 |
| Inventive example 1 | 0.060 | 8.5 | 25 | 0.50 | 5000 | 114 | 52 |
| Inventive example 2 | 0.056 | 7.7 | 34 | 0.67 | 5000 | 113 | 58 |
| Inventive example 3 | 0.053 | 7.3 | 40 | 1.47 | 5667 | 118 | 55 |

As illustrated in Tables 1 and 2, the nonwoven top layer provides excellent resistance to abrasion as evident by the Martindale Abrasion results in terms of mg (per IST 20.5) and abrasion cycles (per ASTM D4966) while simultaneously being porous enough to allow a rapid rate of absorption. Additionally, the through-air-bonded absorbent core layers provide improved absorption and absorption capacity.

For example, Examples 1-3 have absorbed liquid much more rapidly than Comparative Example 1. These desirable aspects illustrated by Examples 1-3 are believed to be related to, at least in part, the combination of the "openness" of the nonwoven top layer and the high void volume of the absorbent core layer. This translates, for example, into a rate of absorption that is less than 5.5 seconds for 1 ml, which is an improvement over Comparative Example 1. This rate of absorption advantage is more greatly highlighted when a volume of 5 ml is used. For instance, the rate of absorption for 5 ml for Examples 1-3 provided a rate that was well below 10 seconds. For Examples 1-3, the run off results were less than 50%. These results provide good indications that fluid will be absorbed rapidly during usage and desirably significantly lowering the risk of fluid spilling outside the absorbent area located around, for example, a fenestration area or covering a tray.

Additionally, Examples 1-3 provided an improved rate of absorption while simultaneously providing a desirably high absorption capacity, such as above 600%. Examples 1-3 also provided at least equivalent resistance to abrasion as illustrated by the Martindale results as per test method ASTM D4966 or test method IST 20.5.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. An absorbent composite, comprising:

(a) a nonwoven top layer comprising hydrophilic fibers;

(b) an absorbent core layer consisting of a plurality of crimped multi-component continuous spunbond filaments directly bonded to the nonwoven top layer via a plurality of ultrasonic bonds or thermal bonds, wherein the absorbent core layer is a high-loft through-air-bonded nonwoven having a basis weight from 10 gsm to 200 gsm; and (c) a water impermeable film, wherein the absorbent core layer is directly sandwiched between the nonwoven top layer and the water impermeable film;

wherein the water impermeable film is extrusion coated directly onto the through-air-bonded nonwoven or adhesively bonded directly onto the through-air-bonded nonwoven;

wherein the absorbent composite includes (i) a composite-run-off value of less than 50% as determined by ISO 9073-11; (ii) a composite-absorption capacity of at least 600% as determined by ISO 9073; and (iii) a composite-rate of absorption of less than 10 seconds for a 5 ml liquid sample as determined by D824-94;

where the high-loft through air bonded nonwoven is a material that is compressible by 20% or more when an applied pressure changes from 0.1 kPa to 0.5k Pa according to BS EN ISO 9703-2 (1995).

2. The absorbent composite of claim 1, wherein the nonwoven top layer comprises a spunbond nonwoven, a meltblown nonwoven, or a combination thereof.

3. The absorbent composite of claim 2, wherein the nonwoven top layer comprises a $S1a$-$M_b$-$S2_c$. structure; wherein 'S1' is a first spunbond material, 'M' is a meltblown material, 'S2' is a second spunbond material, and 'a', 'b', and 'c' indicate the number of respective layers and each independently have a value of 1, 2, 3, 4, or 5.

4. The absorbent composite of claim 1, wherein the nonwoven top layer comprises a carded web comprising staple fibers.

5. The absorbent composite of claim 1, wherein the nonwoven top layer comprises at least 30% by weight of hydrophilic fibers.

6. The absorbent composite of claim 1, wherein nonwoven top layer has an air permeability of at least 100 cubic-feet-per-minute (CFM) as determined by IST 70.1.

7. The absorbent composite of claim 1, wherein the nonwoven top layer includes a-bonding area prior to formation of the absorbent composite from 1% to 30%.

8. The absorbent composite of claim 1, wherein the nonwoven top layer comprises a top-layer-Martindale Abrasion value of less than 2 mg as determined by IST 20.5.

9. The absorbent composite of claim 1, wherein the nonwoven top layer comprises a basis weight from 10-60 grams-per-square-meter (gsm).

10. The absorbent composite of claim 1, wherein the hydrophilic fibers of the nonwoven top layer comprise monocomponent fibers, multicomponent fibers, or a combination thereof.

11. The absorbent composite of claim 1, wherein the plurality of crimped multi-component continuous spunbond filaments comprises at least 30% by weight of hydrophilic fibers.

12. The absorbent composite of claim 1, wherein the plurality of crimped multi-component continuous spunbond filaments comprise bicomponent fibers having a side-by-side configuration including a first component comprising a polyethylene and a second component comprising at least one of a polypropylene or a polyester.

13. The absorbent composite of claim 1, wherein the plurality of crimped multi-component continuous spunbond filaments have an average denier of at most 5 denier.

14. The absorbent composite of claim 1, wherein the absorbent core layer comprises one or more of (i) a void volume greater than 12 cc/g, (ii) an absorbent-core-layer-air permeability below 1600 CFM, and (iii) absorbent-core-layer-absorption capacity that is greater than 1200% as determined by ISO 9073.

15. The absorbent composite of claim 1, wherein the nonwoven top layer and the absorbent core layer are directly or indirectly bonded together via a composite-bonding pattern, wherein the composite-bonding pattern defines a composite-bonding area of no more than 30% of a surface of the absorbent composite.

16. The absorbent composite of claim 1, wherein the absorbent composite comprises one or more of (i) a composite-run-off value of less than 45% as determined by ISO 9073-11, (ii) a composite-absorption capacity of at least 600% as determined by ISO 9073, (iii) a composite-rate of absorption of less than 9 seconds for a 5 ml liquid sample as determined by D824-94, (iv) a composite-void volume of at least 7 g/cc, (v) a composite-Martindale Abrasion value of less than 2 mg as determined by IST 20.5, and (vi) a composite-water-absorption ratio between the weight of water absorbed by the absorbent composite to the dry weight of the composite from 6:1 to 15:1 as determined by ISO 9073.

17. The absorbent composite of claim 1, wherein a first surface of the through-air-bonded nonwoven is directly attached to the nonwoven top layer and a second surface of the through-air-bonded nonwoven is directly attached to the water impermeable film.

18. The absorbent composite of claim 17, wherein the water impermeable film is extrusion coated directly onto the second surface of the through-air-bonded nonwoven.

19. The absorbent composite of claim 17, wherein the water impermeable film is adhesively glued directly onto the second surface of the through-air-bonded nonwoven.

20. The absorbent composite of claim 1, wherein the absorbent core layer is devoid of a cellulosic material.

21. An absorbent composite, comprising:

(a) a nonwoven top layer comprising hydrophilic fibers;

(b) a high-loft through-air-bonded nonwoven comprising a plurality of absorbent core fibers, the high-loft through-air-bonded nonwoven is directly bonded to the nonwoven top layer via a plurality of ultrasonic bonds or thermal bonds, wherein the high-loft through-air-bonded nonwoven consists of crimped continuous fibers, crimped staple fibers, or a combination thereof, and the high lott through-air-bonded nonwoven has a basis weight from 10 gsm to 200 gsm;

(c) a water impermeable film, wherein the through-air-bonded nonwoven is directly sandwiched between the nonwoven top layer and the water impermeable film;

wherein the water impermeable film is extrusion coated directly onto the high-loft through-air-bonded nonwoven; wherein the high-loft through air bonded nonwoven is a material that is compressible by 20% or more when an applied pressure changes from 0.1 kPa to 0.5 kPa according to BS EN ISO 9703-2 (1995), wherein the absorbent composite includes (i) a composite-run-off value of less than 50% as determined by ISO 9073-11; (ii) a composite-absorption capacity of at least 600% as determined by ISO 9073; and (iii) a composite-rate of absorption of less than 10 seconds for a 5 ml liquid sample as determined by D824-94.

22. The absorbent composite of claim 1, wherein the high-loft through-air-bonded nonwoven is from 10 gsm to 25 gsm.

23. The absorbent composite of claim 22, wherein the high-loft through-air-bonded nonwoven consists of the continuous spunbond filaments.

24. The absorbent composite of claim 1, wherein the high-loft through-air-bonded nonwoven has a void volume greater than 12 cc/g.

25. The absorbent composite of claim 1, wherein the water impermeable film is extrusion coated directly onto the through-air-bonded nonwoven.

* * * * *